United States Patent [19]

Reman et al.

[11] Patent Number: 5,041,623

[45] Date of Patent: Aug. 20, 1991

[54] PREPARATION OF ALKYL PROPIONATES

[75] Inventors: Willem G. Reman; Gerben B. J. de Boer; Simon A. J. van Langen; Antonie Nahuijsen, all of Amsterdam, Netherlands

[73] Assignee: Shell Oil Company, Houston, Tex.

[21] Appl. No.: 523,638

[22] Filed: May 15, 1990

[30] Foreign Application Priority Data

Aug. 1, 1989 [GB] United Kingdom ............... 8917579

[51] Int. Cl.$^5$ ............................................. C07C 67/38
[52] U.S. Cl. ................................................... 560/233
[58] Field of Search ......................................... 560/233

[56] References Cited

FOREIGN PATENT DOCUMENTS 106379 4/1984 European Pat. Off. .
235864 9/1987 European Pat. Off. .
279477 8/1988 European Pat. Off. .

Primary Examiner—Michael L. Shippen

[57] ABSTRACT

A continuous process for the preparation of an alkyl propionate, which comprises reacting an alkanol in a liquid phase with ethene in a reaction vessel in the presence of a carbonylation catalyst, and removing alkyl propionate from the reaction vessel in a stream of vapor.

11 Claims, 1 Drawing Sheet

PREPARATION OF ALKYL PROPIONATES

FIELD OF THE INVENTION

The present invention relates to a continuous process for the preparation of alkyl propionates.

BACKGROUND OF THE INVENTION

Alkyl propionates are of interest as solvents, as flavorings and as perfumes. They may be prepared by reacting an alkanol in the liquid phase with ethene and carbon monoxide in a reaction vessel in the presence of a carbonylation catalyst, for example as described in European Patent Application Nos. 0106379, 0235864 and 0279477.

The components of carbonylation catalysts are expensive, and so it is important to minimize the amounts of components consumed per tonne of alkyl propionate produced. Thus, the continuous process described in European Patent Application No. A-0279477 involves a step in which catalyst removed from the reaction vessel during recovery of alkyl propionate is recycled back to the reaction vessel.

The continuous process described in European Patent Application No. 0279477 is relatively complex and, in spite of the catalyst recycle step, consumes relatively large amounts of catalyst components per ton of alkyl propionate produced.

It has now been found that alkyl propionates may be prepared by a carbonylation process in which the amounts of catalyst components consumed are relatively small.

SUMMARY OF THE INVENTION

The present invention provides a continuous process for the preparation of an alkyl propionate, which comprises reacting an alkanol in a liquid phase with ethene and carbon monoxide in a reaction vessel in the presence of a carbonylation catalyst, and removing alkyl propionate from the reaction vessel in a stream of vapor.

The process according to the invention has been found to consume smaller amounts of catalyst components per tonne of alkyl propionate produced than the process described in European Patent Application No. A-0279477.

DESCRIPTION OF THE PREFERRED EMBODIMENTS

Figure 1:
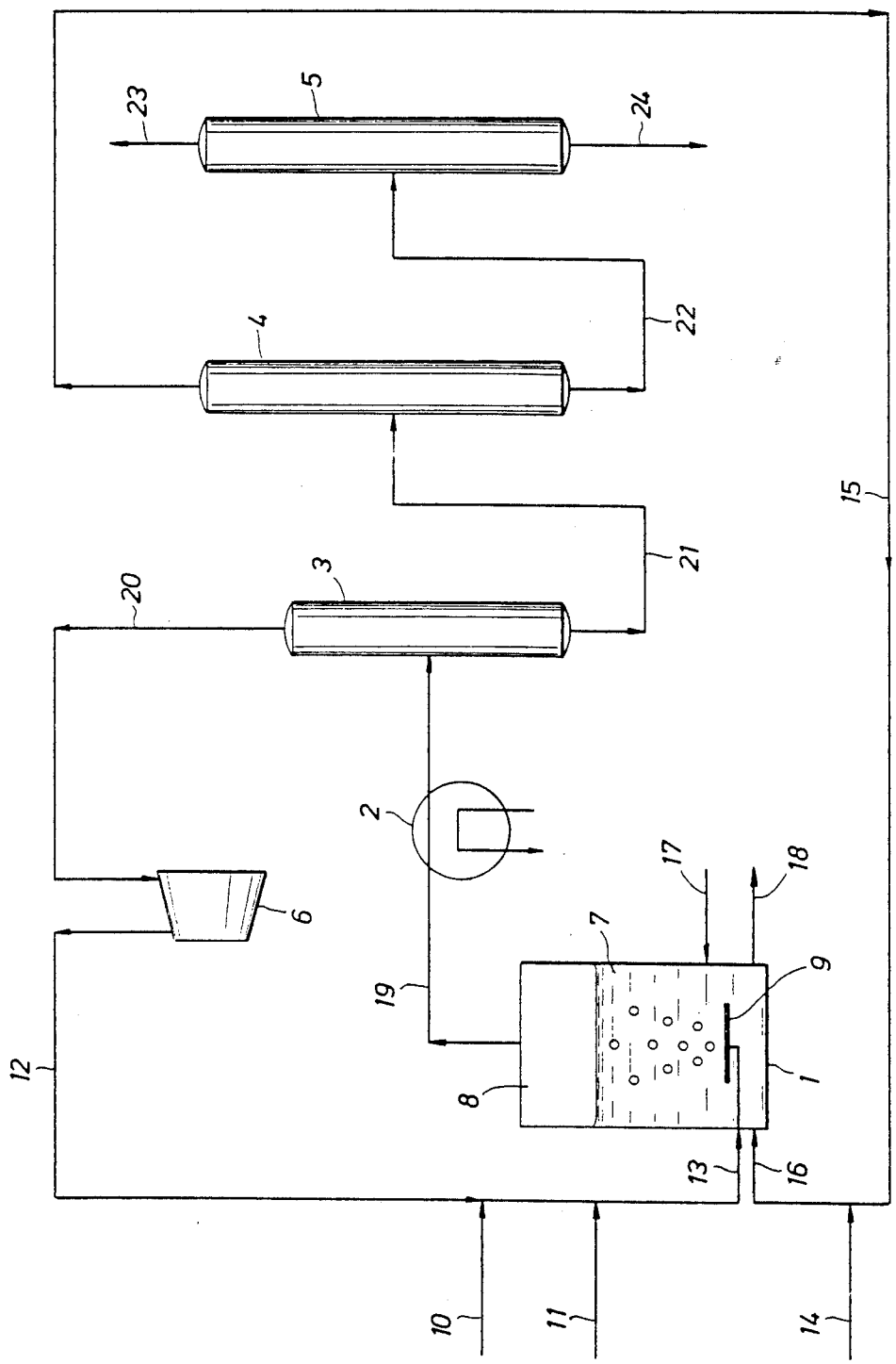
FIG. 1 represents a process flow scheme for the preparation of an alkyl propionate according to the invention.

The vapor stream may be formed by passing a gas through the reaction vessel. The gas strips alkyl propionate from the liquid phase in the reaction vessel and so forms the stream of vapor. Any other volatile materials present in the liquid phase, for example alkanol, will also be removed in the stream of vapor. Accordingly, the stream of vapor comprises alkyl propionate, gas, and alkanol.

The rate at which gas is passed through the reaction vessel should be sufficient to strip alkyl propionate from the liquid phase. It may be determined by simple experimentation.

The gas used to form the stream of vapor may be blown onto the surface of the liquid phase, but is preferably bubbled through it. When gas is bubbled through the liquid phase, it stirs the liquid phase. In this case, a mechanical stirrer is generally not required. Preferably, ethene and carbon monoxide are bubbled through the liquid phase.

The gas used to form the stream of vapor may comprise ethene, carbon monoxide and/or one or more inert gases, for example nitrogen, carbon dioxide and noble gases such as argon. Preferably, the gas consists substantially of ethene and carbon monoxide.

The molar ratio of ethene to carbon monoxide is preferably in the range of from 9:1 to 1:9, more preferably from 2:1 to 1:2, and most preferably about 1:1.

The process may be performed in the presence of a solvent, but is preferably not.

The carbonylation catalyst may be any carbonylation catalyst that gives an acceptable reaction rate under the conditions prevailing in the reaction vessel. Examples of suitable catalysts may be found in European Patent Application Nos. 0106379, 0235864 and 0279477.

In one preferred class of carbonylation catalysts, the catalyst comprises a palladium compound, a ligand and a protonic acid.

The palladium compound may be a salt of palladium, for example a salt with nitric acid, sulfuric acid, a hydrohalic acid or a carboxylic acid such as acetic acid, or a complex of palladium such as palladium acetylacetonate, tetrakistriphenylphosphine palladium, bis-tri-o-tolylphosphine palladium acetate or bis-triphenylphosphine palladium sulfate.

The number of gram atoms of palladium used per mole of ethene is not critical. Preferably it is in the range of from $10^{-5}$ to $10^{-1}$.

The ligand may be a phosphorus-, arsenic- or antimony-containing ligand. Preferably the ligand is a phosphine. Particularly preferred ligands are triaryl phosphines, for example phosphines of the general formula $PR^1R^2R^3$ in which each of $R^1$, $R^2$ and $R^3$ represents an aryl group (e.g. phenyl). It is understood that the term "aryl group", as used herein, refers to unsubstituted aryl groups as well as aryl groups which are substituted by one or more substituents selected from halogen atoms and alkyl, aryl, alkoxy, carboxy, acyl, trihalomethyl, cyano, dialkylamino, sulfonylalkyl and alkanoyloxy groups. Examples of suitable phosphines are tri-p-tolylphosphine, tri-p-methoxyphosphine and triphenylphosphine.

When a phosphine ligand is used, it is preferably present in an amount of at least 5 moles per gram atom of palladium, more preferably at least 10 moles per gram atom. The concentration of phosphine is preferably at least 10 mmoles per liter, more preferably at least 20 mmoles per liter.

The protonic acid preferably has a non-coordinating anion, by which is meant that little or no co-valent interaction takes place between palladium and the anion. Typical examples of such anions are $PF_6^-$, $SbF_6^-$, $BF_4^-$ and $ClO_4^-$.

The protonic acid is preferably selected from sulfuric acid; sulfonic acids such as fluorosulfonic acid, chlorosulfonic acid, 2-hydroxypropane-2-sulfonic acid, p-toluenesulfonic acid, methanesulfonic acid and trifluoromethanesulfonic acid; perhalic acids such as perchloric acid; 2,6-disubstituted benzoic acids such as 2,6-dichlorobenzoic acid; phosphoric acid; phosphonic acids such as benzenephosphonic acid and 2-bromobenzenephosphonic acid; arsenic acid; and complexes of HF with fluorine-containing Lewis acids such as $BF_3$, $SiF_4$, $SbF_5$, $PF_5$, $TaF_5$ and $NbF_5$.

The acid is preferably used in an amount in the range of from 1 to 50 moles per gram atom of palladium.

When a carbonylation catalyst comprising a palladium compound, a phosphine and a protonic acid is used in the process according to the invention, phosphine and protonic acid are preferably supplied intermittently, more preferably continuously to the reaction vessel, in order to maintain constant catalyst activity.

The ratio of the molar amounts of ligand and acid added during the reaction period may conveniently range from about 0.75 to about 3.5. At the beginning of the reaction, the molar ratio will normally be in the range of from about 1 to about 3.5, and during the reaction, the molar ratio of the added ligand and acid will conveniently be in the range of from about 0.75 to about 1.25, and is preferably about 1.

The pressure and temperature within the reactor are chosen so as to maintain sufficient alkanol in the liquid phase in the reaction vessel, and yet allow alkyl propionate to be removed in a stream of vapor. In general, the temperature in the reaction vessel is in the range of from about 80° C. to about 125° C., preferably from about 90° C. to about 120° C., more preferably 110° C. The pressure in the reaction vessel is conveniently in the range of from about 5 to about 20 bar, preferably from about 8 to about 12 bar.

The alkanol used in the process according to the invention is preferably a $C_{1-6}$ alkanol, more preferably a $C_{1-4}$ alkanol. Specific examples of alkanols are methanol, 2-propanol and 1-butanol. Preferably the alkanol is methanol, in which case the alkyl propionate produced is methyl propionate.

The stream of vapor leaving the reaction vessel may be cooled to afford a gas phase and a liquid phase. The gas phase may conveniently be recycled back to the reaction vessel. Alkyl propionate may be recovered from the liquid phase by distillation. Unreacted alkanol recovered from the liquid phase may be recycled back to the reactor.

When a mixture of methyl propionate and methanol is subject to distillation, an azeotropic mixture of methyl propionate and methanol is formed. This mixture is very conveniently recycled back to the reaction vessel.

DETAILED DESCRIPTION OF THE DRAWING

The invention will now be described in more detail, by way of example with reference to the accompanying drawing (FIG. 1) which represents a simplified process flow scheme for the preparation of an alkyl propionate.

FIG. 1 shows a reaction vessel (1), a condenser (2), a gas/liquid separator (3), first and second distillation columns (4 and 5), a gas compressor (6) and flow lines (10 to 24).

The reaction vessel (1) contains a liquid phase (7) and a vapor phase (8). The internal volume of the reaction vessel is 600 ml. The volume of the liquid phase in the reaction vessel is kept at a constant 400 ml using a level controlling device (not shown).

The liquid phase comprises alkanol, alkyl propionate and a carbonylation catalyst which comprises palladium acetate, triphenylphosphine and methane sulfonic acid.

Ethene, supplied via lines (10) and (13), carbon monoxide supplied via lines (11) and (13), and recycled gas, supplied via lines (12) and (13), enter the liquid phase (7) in the reaction vessel (1) through a sparger (9) and bubble through to the vapor phase (8). The bubbles of gas stir the liquid phase as they rise.

Fresh and recycled alkanol supplied via lines (14) and (15) enter the reaction vessel via line (16). Triphenylphosphine and methane sulfonic acid are continuously supplied to the reaction vessel via line (17) at a rate sufficient to maintain constant catalyst activity. A small heavy ends bleed is taken from the reaction vessel via line (18). A very small quantity of palladium acetate is also added continuously to the reaction vessel via line (17) to make up for losses through the bleed.

A vapor stream, comprising alkyl propionate and alkanol, passes via line (19) through condenser (2) to gas/liquid separator (3). Separated gas is conducted via line (20) to compressor (6) and then via line (12) back to the reaction vessel.

Separated liquid is conducted via line (21) to first distillation column (4). The top product comprising unreacted alkanol is recycled to the reaction vessel via line (15). When the alkanol is methanol, the top product is an azeotropic mixture of methanol and methyl propionate.

The bottom product from the first distillation column (4) is conducted via line (22) to second distillation column (5), from which pure alkyl propionate is removed as top product via line (23), and heavy ends as bottom product via line (24).

Table 1 below details the process conditions and results of a 500-hour run using methanol as the alkanol.

TABLE I

| | |
|---|---|
| Temperature | 100° C. |
| Pressure | 11 bar |
| Gas flow (CO and ethene) (molar ratio 1:1) | 110 Nl/h |
| Gas conversion per pass | 10–15% |
| Methanol level | 18 w % |
| Methanol conversion per pass | 25–30% |
| Stripping efficiency | 100% |
| Initial concentrations of: | |
| palladium acetate | 2.2 mmol/l |
| triphenylphosphine | 45 mmol/l |
| methane sulfonic acid | 13 mmol/l |
| Triphenylphosphine consumption | 1.6 kg/ton |

From Table I, the ligand consumption is 1.6 kg/ton. This may be compared with a figure of 2.9 kg/ton, which may be calculated from the data given in the example of European Patent Application No. 0279477. Thus the process achieves a reduction of ligand consumption in excess of 40% compared with the known process.

2-Propyl propionate and 1-butyl propionate were prepared from 2-propanol and 1-butanol using procedures similar to that described above. In each case the run length was 75 hours. The runs were performed for the purpose of demonstrating that alkyl propionates other than methyl propionate can be prepared by the process according to the invention. Table II gives details of the process conditions and the results.

TABLE II

| Alkanol | 2-propanol | 1-butanol |
|---|---|---|
| Temperature | 115–120° C. | 110–115° C. |
| Pressure | 11 bar | 7 bar |
| Gas flow (CO and ethene) (molar ratio 1:1) | 30–25 Nl/h | 40 Nl/h |
| Alkanol level | 20% w | 20% w |
| Stripping efficiency | 95% | 93% |
| Initial concentrations of: | | |

TABLE II-continued

| | | |
|---|---|---|
| palladium acetate | 1 mmol/l | 2 mmol/l |
| triphenylphosphine | 50 mmol/l | 50 mmol/l |
| methane sulfonic acid | 20 mmol/l | 20 mmol/l |
| Triphenylphosphine consumption | 5.5 kg/ton | 3.3 kg/ton (0-19 hrs) 6.8 kg/ton (19-43 hrs) |
| Rate of production of alkyl propionate | about 350 mol/molPd/hr | initially 500 mol/molPd/hr falling to 100 mol/molPd/hr during first 20 hrs, then remaining substantially constant |

What is claimed is:

1. In a continuous process for the preparation of an alkyl propionate, which comprises reacting an alkanol in a liquid phase with ethene and carbon monoxide in a reaction vessel in the presence of a carbonylation catalyst, the improvement which comprises passing a gas through said reaction vessel thereby stripping alkyl propionate from the liquid phase and forming a stream of vapor comprising alkyl propionate, gas and alkanol, and thereafter removing alkyl propionate from the reaction vessel in said stream of vapor.

2. The process of claim 1 wherein ethene and carbon monoxide are bubbled through the liquid phase.

3. The process of claim 1 wherein said carbonylation catalyst comprises a palladium compound, a ligand and a protonic acid.

4. The process of claim 3 wherein said ligand is a triarylphosphine present in an amount of at least 5 moles per gram atom of palladium.

5. The process of claims 3 or 4 wherein said protonic acid is selected from the group consisting of sulfuric acid, sulfonic acids, perhalic acids, 2,6-disubstituted benzoic acids, phosphoric acid, phosphonic acids, arsenic acid and complexes of HF with fluorine-containing Lewis acids.

6. The process of claim 4 wherein the phosphine and protonic acid are supplied continuously to the reaction vessel.

7. The process of claim 1 wherein the pressure in the reaction vessel is in the range of from 8 bar to 12 bar.

8. The process of claim 1 wherein the reaction temperature is in the range of from 90° C. to 120° C.

9. The process of claim 1 wherein said alkanol is selected from the group consisting of methanol, 2-propanol, and 1-butanol.

10. The process of claim 9 wherein the alkanol is methanol.

11. The process of claim 10 wherein the stream of vapor is cooled to afford a gas phase and a liquid phase, and wherein the gas phase is recycled back into the reaction vessel, and an azeotropic mixture of methanol and methyl propionate is distilled off from the liquid phase, condensed, and recycled back into the reaction vessel.

* * * * *